(12) United States Patent
Deac (10) Patent No.: US 9,675,263 B2
(45) Date of Patent: Jun. 13, 2017

(54) RETRACTABLE MAPPING JACKET

(71) Applicant: MEDTRONIC CRYOCATH LP, Toronto (CA)

(72) Inventor: Ioana Alina Deac, Vaudreuil-Dorion (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 641 days.

(21) Appl. No.: 13/775,322

(22) Filed: Feb. 25, 2013

(65) Prior Publication Data
US 2014/0243642 A1 Aug. 28, 2014

(51) Int. Cl.
*A61B 18/18* (2006.01)
*A61B 5/0408* (2006.01)
(Continued)

(52) U.S. Cl.
CPC ........ *A61B 5/04085* (2013.01); *A61B 5/0422* (2013.01); *A61B 18/1492* (2013.01); *A61B 2018/00023* (2013.01); *A61B 2018/00839* (2013.01); *A61B 2018/0212* (2013.01); *A61B 2018/1475* (2013.01); *A61B 2562/222* (2013.01); *A61B 2562/227* (2013.01)

(58) Field of Classification Search
CPC ...... A61B 18/1492; A61B 2018/00577; A61B 2218/002; A61B 2018/00351; A61B 2018/00214; A61B 18/1206; A61B 2018/1467; A61B 5/6852; A61M 25/0133; A61M 25/007; A61M 25/0071; A61M 25/01; A61M 2025/0675; A61M 2025/0681; A61M 25/00

USPC ........ 600/372–374, 377, 393, 435, 466–467, 600/481, 508–509; 604/103.06; 606/22–42; 607/119, 122–123
See application file for complete search history.

(56) References Cited

U.S. PATENT DOCUMENTS 5,637,090 A * 6/1997 McGee ................ A61B 5/0422
600/374
6,771,996 B2 * 8/2004 Bowe et al. .................. 600/374
(Continued)

OTHER PUBLICATIONS

International Search Report and Written Opinion dated Apr. 8, 2014 for International Application Serial No. PCT/CA2014/000010, International Filing Date: Jan. 10, 2014 consisting of 13 pages.

*Primary Examiner* — Joseph Stoklosa
*Assistant Examiner* — Brian M Antiskay
(74) *Attorney, Agent, or Firm* — Christopher & Weisberg, P.A.

(57) ABSTRACT

An accessory and system to provide a medical device with mapping and ablation functionality. The system may include an ablation device with a handle, a treatment element, and an elongate body. The ablation element may be located on the elongate body distal portion, and a mapping sleeve may be disposable about at least part of the distal portion of the ablation device and may include mapping electrodes disposed on the outer surface. The mapping sleeve proximal region may include a retraction element defining a proximal end and a distal end, the distal end being coupled to the proximal region of the mapping sleeve, such that retracting the retraction element toward the elongate body proximal portion pulls the mapping sleeve away from the treatment element of the ablation device.

7 Claims, 6 Drawing Sheets

(51) Int. Cl.
    *A61B 18/14*     (2006.01)
    *A61B 5/042*     (2006.01)
    *A61B 5/04*     (2006.01)
    *A61B 18/00*     (2006.01)
    *A61B 18/02*     (2006.01)

(56) References Cited

U.S. PATENT DOCUMENTS

| | | |
|---|---|---|
| 6,858,026 B2 | 2/2005 | Sliwa, Jr. et al. |
| 7,824,403 B2 | 11/2010 | Vaska et al. |
| 8,114,069 B2 | 2/2012 | Sliwa, Jr. et al. |
| 2010/0137700 A1* | 6/2010 | Passman et al. ............. 600/374 |
| 2010/0249568 A1* | 9/2010 | Stehr et al. .................. 600/374 |
| 2012/0053581 A1* | 3/2012 | Wittkampf et al. ............ 606/41 |
| 2014/0275913 A1* | 9/2014 | Hill et al. ..................... 600/373 |

* cited by examiner

RETRACTABLE MAPPING JACKET

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a device and system for integrating ablation and mapping functionality into a single medical device. In particular, the present invention relates to a cost-effective accessory that adds mapping functionality to an ablation device after production.

BACKGROUND OF THE INVENTION

Catheter ablation is commonly used to treat a variety of cardiovascular conditions, such as cardiac arrhythmias, atrial fibrillation, and other irregularities in the transmission of electrical impulses through the heart. This minimally invasive surgical technique may involve the use of tip electrodes or other ablating elements to create lesions or other anatomical effects that disrupt or block electrical pathways through the targeted tissue. In the treatment of cardiac arrhythmias, a specific area of cardiac tissue having aberrant electrical activity (e.g. focal trigger, slow conduction, excessively rapid repolarization, fractionated electrogram, etc.) is typically identified first before subsequent treatment.

It is advantageous to identify an optimal ablation site before ablating the tissue. Presently, this procedure may require mapping an area of tissue with a first mapping device. Once an optimal ablation site is identified, the mapping device is withdrawn and replaced with an ablation device. However, this practice may increase the chances of patient injury or procedure complications, and may disadvantageously increase the total time needed to treat a condition. Alternatively, presently know devices may include mapping and ablation functionality in a single device, which may reduce procedure time and complexity by eliminating the need to employ separate mapping and ablation devices for each task. Combination mapping and ablation devices also increase ablation accuracy, because once aberrant tissue (the "target tissue") is found, ablation can begin immediately without having to remove the mapping device and relocating the target tissue with the ablation device. However, such devices may require complicated manufacturing steps and expensive materials, may present insulation problems between mapping and ablation electrodes, and may be prohibitively expensive for some surgeons.

It is therefore desirable to provide a system and device for performing both mapping and ablation at a reduced cost over presently known devices. It is further desirable to provide mapping and ablation functionality in a single device that is easy to operate and cost-effective to manufacture.

SUMMARY OF THE INVENTION

The present invention advantageously provides a medical device accessory and system with mapping and ablation functionality. The accessory may generally include a resilient sleeve defining an inner surface and an outer surface, and a mapping electrode disposed on the outer surface of the resilient sleeve. The resilient sleeve may define a proximal portion and a distal portion, and the proximal portion may define a proximal edge and the distal portion defining a distal tip including an aperture. The resilient sleeve may further include a retraction element coupled to the proximal portion of the resilient sleeve. Additionally, the device may comprise an electrode wire in electrical communication with the mapping electrode. The wire may be fused to the inner surface of the resilient sleeve. The resilient sleeve may define a primary lumen and a secondary lumen, each having a longitudinal axis, and the secondary lumen may be disposed within the primary lumen, such that the longitudinal axes of the primary and secondary lumens are substantially parallel. The resilient sleeve may include a plurality of coextruded layers, and the wire may be disposed between two coextruded layers. Further, the proximal portion of the resilient sleeve may include a proximal edge, and the retraction element may be coupled to the proximal edge and extend for a distance that is uncoupled from the proximal edge. The retraction element may define a lumen, the wire being disposed within the lumen. The accessory may further include a plurality of mapping electrodes and a plurality of electrode wires. For example, the plurality of wires may be composed of a conductive material that is printed onto the outer surface of the resilient sleeve.

The system may generally include an ablation device including an ablation element and an elongate body defining a distal portion, a proximal portion, and a longitudinal axis, the ablation element being located on the distal portion of the elongate body, a resilient mapping sleeve disposable about at least the ablation element of the distal portion of the ablation device, the mapping sleeve defining an inner surface, an outer surface, and a primary lumen having a longitudinal axis. The system may further include a power generator and a plurality of mapping electrodes disposed on the outer surface of the mapping sleeve, each of the plurality of mapping electrodes including an electrode wire that is coupled directly to the power generator. Pulling the mapping sleeve toward the proximal portion of the elongate body pulls the mapping sleeve away from the ablation element, thereby exposing it in order to ablate target tissue. The mapping sleeve may further define a proximal region and a distal region including an exit opening sized to allow at least a portion of the distal portion of the elongate body to pass therethrough. The mapping sleeve may further define a retraction element, the retraction element being coupled to the proximal portion of the mapping sleeve. Exerting a pull force on the retraction element may retract the mapping sleeve toward the proximal region of the elongate body and expose the ablation element. At least a region of the elongate body and the treatment element may protrude from the exit opening of the mapping sleeve when the mapping sleeve is retracted. The mapping sleeve may further define a secondary lumen having a longitudinal axis, and the longitudinal axes of the primary lumen and secondary lumen may be substantially parallel. Each of the plurality of mapping electrodes may include an electrode wire, and the plurality of electrode wires may be coupled to an inner surface of the mapping sleeve primary lumen, printed onto the outer surface of the mapping sleeve, or disposed within the secondary lumen.

In another embodiment, the system may include an ablation device including a handle, a treatment element, and an elongate body defining a distal portion, a proximal portion, and a length, the ablation element being located on the distal portion of the elongate body, a mapping sleeve disposable about at least the treatment element, the mapping sleeve having a length that is less than the length of the elongate body, a plurality of mapping electrodes disposed on the outer surface of the mapping sleeve, and a retraction element defining a proximal end and a distal end, the distal end being coupled to the proximal region of the mapping sleeve, retraction of the retraction element toward the handle pulling the mapping sleeve away from and exposing the treatment element of the ablation device.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
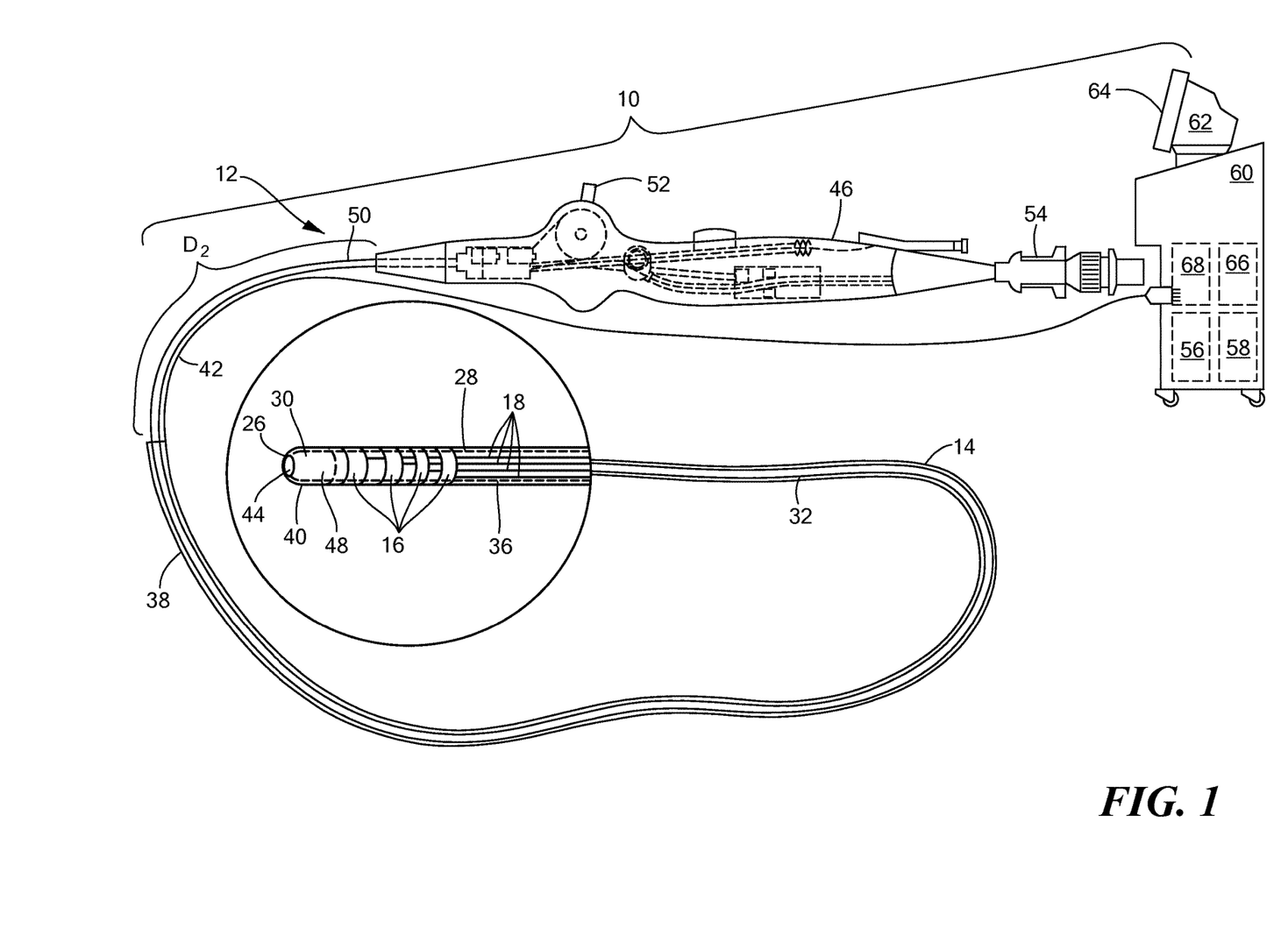
FIG. 1 shows a first embodiment of a system including a mapping sleeve and an ablation device according to the present invention.
Figure 6:
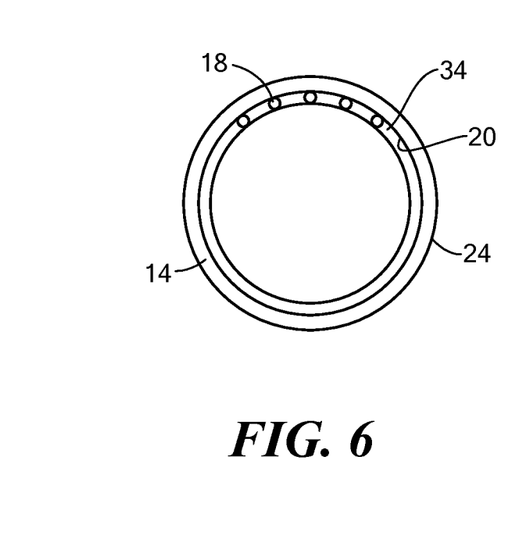
FIG. 6 shows a cross-sectional view of a first embodiment of a mapping sleeve.
Figure 7:
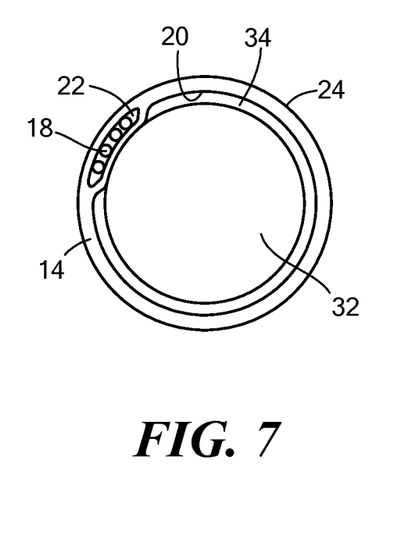
FIG. 7 shows a cross-sectional view of a second embodiment of a mapping sleeve.
Figure 8:
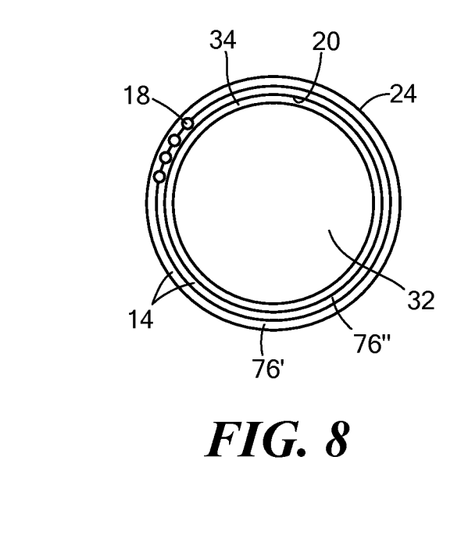
FIG. 8 shows a cross-sectional view of a third embodiment of a mapping sleeve.

Referring now to FIG. 1, a system 10 that includes a treatment device 12 and a device accessory 14 is shown. The device accessory may be a mapping jacket or sleeve 14 on which one or more mapping electrodes 16 are borne. For example, the mapping electrodes 16 may be suitable for recording electrocardiogram signals within cardiac tissue. The mapping electrodes 16 may be composed of an electrically conductive material that is affixed to, fused with, or printed onto the mapping sleeve 14. Further, the mapping electrodes 16 may be ring or band electrodes (as shown in FIG. 1). Each mapping electrode 16 may include an electrode wire 18. The wires 18 may be affixed to or fused with the mapping sleeve 14 (for example, an inner surface 20 of the sleeve 10), and the wires 18 contained between the mapping sleeve 14 and device 12 (as shown in FIG. 6), contained within a lumen 22 of the mapping sleeve (as shown in FIG. 7), or disposed between two extrusion layers of the mapping sleeve (as shown in FIG. 8). Alternatively, the wires 18 may be composed of a conductive material that is printed on the outer surface 24 of the sleeve (as shown in FIG. 1). The mapping sleeve 14 may be composed of a soft, flexible, resilient, biocompatible material, such as nylon, Pebax, silicone, or polyvinylchloride (PVC).

The mapping sleeve 14 may be substantially tube shaped with a substantially closed distal tip 26. That is, the mapping sleeve 14 may have a primary lumen 28 within which at least a portion of the device 12 may be inserted, the distal tip 26 of the sleeve 14 being proximate the distal tip 30 of the device 12. The inner diameter of the primary lumen 28 may be sufficient to accommodate the device 12 within the sleeve 14. For example, the sleeve 14 may be configured to fit over an elongate body 32 of a device 12 with a 7 French diameter. Further, there may be a small gap 34 between an inner surface 20 of the sleeve 14 and the elongate body 32 so that the sleeve 14 may be smoothly retracted without putting strain on the distal region 36 of the device 12 (for example, as shown in FIGS. 6-8). However, the gap 34 may be thin enough that the sleeve 14 is not pulled from the device 12 as the device 12 is navigated to the target tissue. The mapping sleeve 14 may define a proximal region 38 and a distal region 40, and may include one or more cables, cords, wires, or other retraction elements 42 (as shown and described in more detail in FIG. 9). The distal tip 26 of the mapping sleeve 14, although substantially closed, may be configured to allow the device 12 to pass therethrough when the mapping sleeve 14 is retracted (for example, as shown and described in more detail in FIGS. 4 and 5). That is, the distal tip 26 of the mapping sleeve 14 may include an aperture or opening 44. In an alternative embodiment shown and described in FIGS. 10 and 11, the mapping sleeve 14 may be integrated with the device 12 from a handle 46 of the device 12 to a distance $D_1$ from the distal tip 30 of the device 12. Along this distance $D_1$ to the distal tip 30 of the device 12, the mapping sleeve 14 may not be integrated with the device 12 but may be configured as a separate sleeve disposed about at least a portion of the distal portion 36 of the device 12.

The mapping sleeve 14 may be a distance $D_2$ shorter than the elongate body 32 of the device 12, so that the sleeve 14 may be retracted away from one or more treatment elements 48 at the distal region 36 of the elongate body 32. As a non-limiting example, the sleeve 14 may be between at least approximately 5 inches and approximately 6 inches shorter than the elongate body 32 of the device, and may be up to 15 inches or more, as long as the sleeve 14 may be retracted away from the distal region 36 of the elongate body 32 without becoming bunched at the proximal region 50 of the elongate body 32 where it joins the handle 46. Further, at least a portion of the mapping sleeve 14 may remain outside of the patient throughout the mapping and ablation procedures. As a non-limiting example, a typical 7-French focal catheter may have a usable length of approximately 108.5 cm. A mapping sleeve 14 used with such a catheter 12 may be approximately 70 cm. The distance $D_2$, 38.5 cm (approximately 15 in), by which the sleeve 14 is shorter than the elongate body 32 may be used to retract the mapping sleeve 14 toward the handle 46. At least a portion of the proximal region 38 of the sleeve 14 may remain outside of the patient during mapping and treatment (for example, ablation) procedures. For example, at least a portion of the proximal region 38 of the sleeve 14 may extend from an incision made in a patient to allow femoral, radial, or brachial access to the device 12.

The system 10 may be used with a device such as a focal catheter used for cryoablation or other types of ablation including radiofrequency (RF), ultrasound, microwave, and/or ultrasound ablation. The catheter 12 may include an elongate body 32 defining a proximal region 50, a distal region 36, and one or more lumens therebetween, such as fluid, mechanical, or electrical lumens (not shown). The elongate body 32 may be passable through a patient's vasculature and/or proximate to a tissue region for diagnosis or treatment, such as a catheter, sheath, or intravascular introducer. The elongate body 32 may include one or more bellowed regions or it may have a smooth outer surface. Further, the elongate body distal region 36 may include one or more treatment elements 48 such as treatment electrodes and/or thermal exchange areas. As a non-limiting example, the distal tip 30 of the elongate body 32 may be composed of a thermally conductive material such as metal. A refrigerant may be circulated within the distal tip 30, and the cooled tip used to cryoablate target tissue. Further, the treatment electrodes 48 may be used to apply RF, ultrasound, microwave, or other ablation energy, or to apply high voltage energy to electroporate target tissue.

The catheter 12 may include a handle 46 coupled to the proximal region 50 of the elongate body 32. The handle 46 may include one or more actuators, wheels, knobs, or other steering control elements 52 for steering the device 12. In an alternative embodiment, the actuators 52 of the handle may be used to retract the mapping sleeve 14. Further, the handle 46 may include circuitry for identification and/or use in controlling of the medical device or another component of the system. For example, the handle 46 may include one or more pressure sensors to monitor the fluid pressure within the catheter. The handle 46 may also include connectors 54 that are matable directly to a fluid reservoir 56, fluid recovery reservoir 58, and/or console 60 or indirectly by way of one or more umbilicals. The handle 46 may further include blood detection circuitry in fluid and/or optical communication with one or more fluid delivery pathways throughout the system. The handle 46 may also include a pressure relief valve in fluid communication with the one or more fluid pathways to automatically open under a predetermined threshold value in the event that value is exceeded.

The console 60 may include one or more computers 62, each having a display 64, one or more user input devices, and one or more processors for executing algorithms, programs, and/or calculations, and for generating images, alerts, maps, instructions, system feedback or status signals, and/or user input options on the display. The system 10 may further include one or more coolant reservoirs 56, coolant recovery reservoirs 58, power sources 66, energy generators 68, and/or vacuum pumps for evacuating expanded coolant from the device distal region 36. The system 10 described herein may be configured to deliver one or a combination of energy modalities, for example, radiofrequency energy, microwave energy, ultrasound energy, cryoablation, electroporation, and combinations thereof. Further, the system 10 and device 12 may be configured to deliver one or more treatment agents (for example, genes, proteins, or other substances that affect cells of the target tissue).

Figure 2:
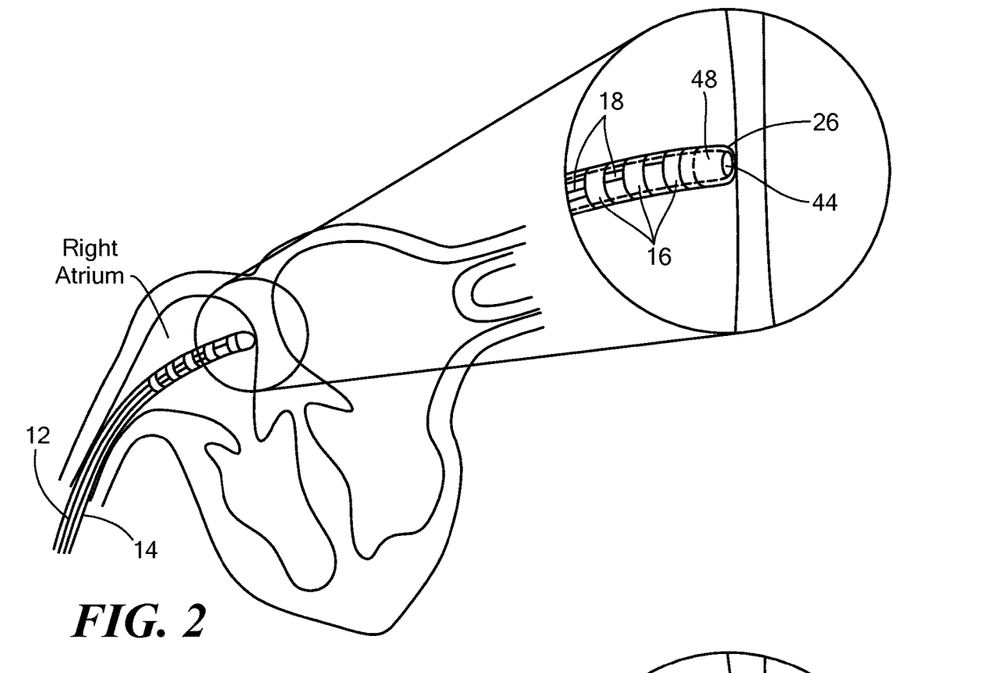
FIG. 2 shows a treatment device including a mapping sleeve disposed over at least a portion of the distal region of the treatment device, such that a treatment element is covered by the mapping sleeve.
Figure 3:
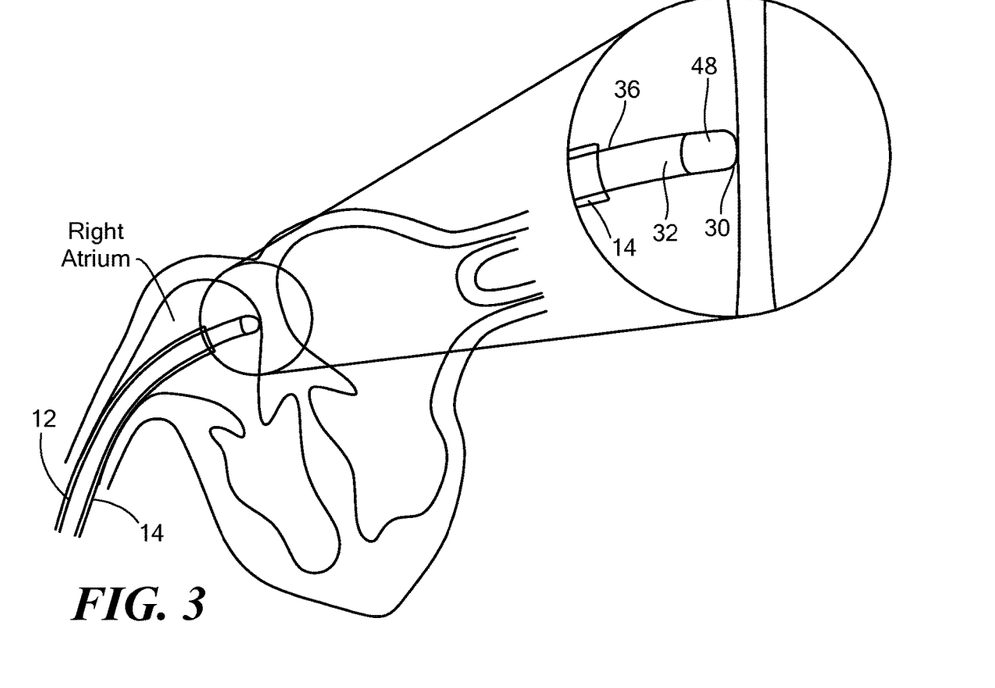
FIG. 3 shows the treatment device of FIG. 2 with the mapping sleeve retracted to expose the treatment element.

Referring now to FIGS. 2 and 3, a treatment device 12 including a mapping sleeve 14 disposed over at least a portion of the distal region 36 of the treatment device 12 is shown, the mapping sleeve 14 covering a treatment element 48 of the device 12 and retracted to expose the treatment element 48, respectively. FIGS. 2 and 3 show the device 12 with mapping sleeve 14 disposed within the right atrium of the heart, although it will be understood that the device may be used to map other anatomical features and other areas within the heart. A close-up view of the device 12 with sleeve 14 is shown in the inset of each figure. The mapping sleeve 14 may be disposed about all or at least a portion of the distal region 36 of the elongate body 32 of the device 12. In an alternative embodiment, as shown and described in FIGS. 10 and 11, the mapping sleeve 14 may be integrated with the ablation device 12 from the proximal region 50 of the elongate body 32 at the handle 46 to a location within the distal region 36 of the elongate body 32 but a distance $D_1$ from the distal tip 30 of the elongate body 32. The device 12 may be delivered to a target area of tissue with the mapping sleeve 14 being disposed about the elongate body 32 (as shown in FIG. 2). Once the mapping electrodes 16 are in contact with the target tissue, the mapping electrodes 16 may be activated to record cardiac electrical signals, such as electrocardiogram (ECG) signals. Alternatively, the mapping electrodes 16 may passively record signals such as monophasic action potential signals. The device 12 may be moved to a new area of target tissue and the new area mapped, until a target treatment site is identified. Once the target treatment site is identified, a user (for example, a surgeon) may pull on portion of the proximal region 38 of the mapping sleeve 14 that is external to the patient and/or the retraction elements 42 to manually retract the mapping sleeve 14. Alternatively, the user may manipulate one or more controls 52 within the handle 46 of the device 12 to retract the mapping sleeve 14, if the one or more retraction elements 42 are in communication with the handle 46. Retraction of the sleeve 14 exposes one or more treatment elements 48 (as shown in FIG. 3). For example, once the sleeve 14 is retracted from the distal tip 30 of the elongate body 32, the device 12 may be activated to ablate or treat the tissue. Further, the treatment and/or ablation portions of the device 12 may have a larger "footprint" than the mapping portions of the sleeve. It may be desirable to use the sleeve 14 with a device 12 having a large treatment element 48 or large area over which multiple treatment elements 48 are arranged, thus being able to create a large lesion in the tissue at the treatment site. In this case, the mapping sleeve 14 may provide mapping functionality without sacrificing space on or within the device 12 that would otherwise be dedicated to treatment elements. Further, the mapping electrodes 16 may have less spacing between them than do the ablation elements 48, which may enhance the quality of recorded mapping signals.

Figure 4:
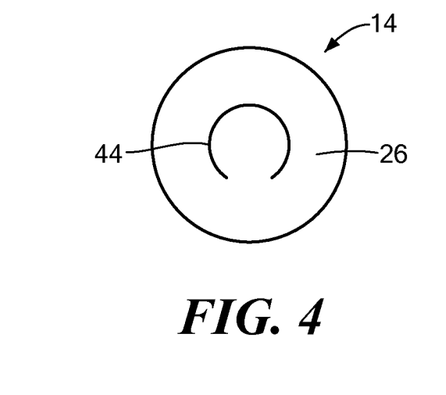
FIG. 4 shows a first embodiment of a distal tip of a mapping sleeve.
Figure 5:
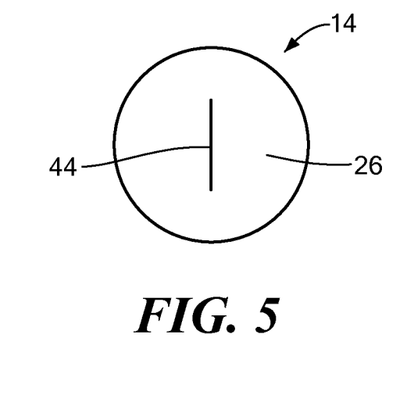
FIG. 5 shows a second embodiment of a distal tip of a mapping sleeve.

Referring now to FIGS. 4 and 5, a first and second embodiment of a distal tip 26 of the mapping sleeve 14 are shown. As shown and described in FIGS. 2 and 3, the mapping sleeve 14 may be retracted from the distal region 36 of the elongate body 32 of the device to expose one or more treatment elements 48 for treating tissue. Accordingly, the distal dip 26 of the sleeve 14 may include an aperture or opening 44 through which the device may be passed. As non-limiting examples, FIG. 4 shows a slit-type opening 44 and FIG. 5 shows a flap-type opening 44. Additionally, a hole-type opening 44 is shown in FIG. 1. No matter the shape or structure of the opening 44, the stretchable, resilient, and flexible nature of the sleeve 14 may allow a device 12 to pass through the opening 44 that has a diameter that is approximately the same as, or up to several times greater than, the diameter of the opening 44. Additionally, the configuration of the opening 44 (for example, the slit-type or flap-type opening) may maintain a substantially closed configuration when disposed about the distal region 36 of the elongate body 32, only opening when the sleeve 14 is retracted to allow the device 12 to pass through.

Figure 9:
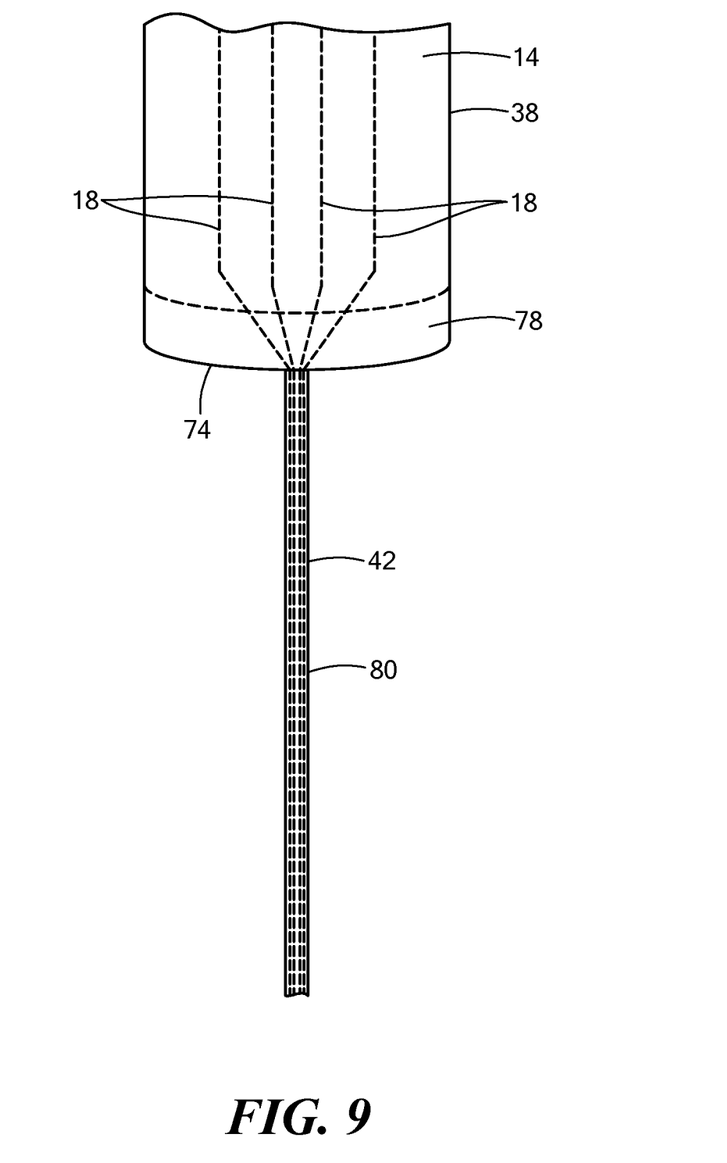
FIG. 9 shows a proximal region of a mapping sleeve.
Figure 10:
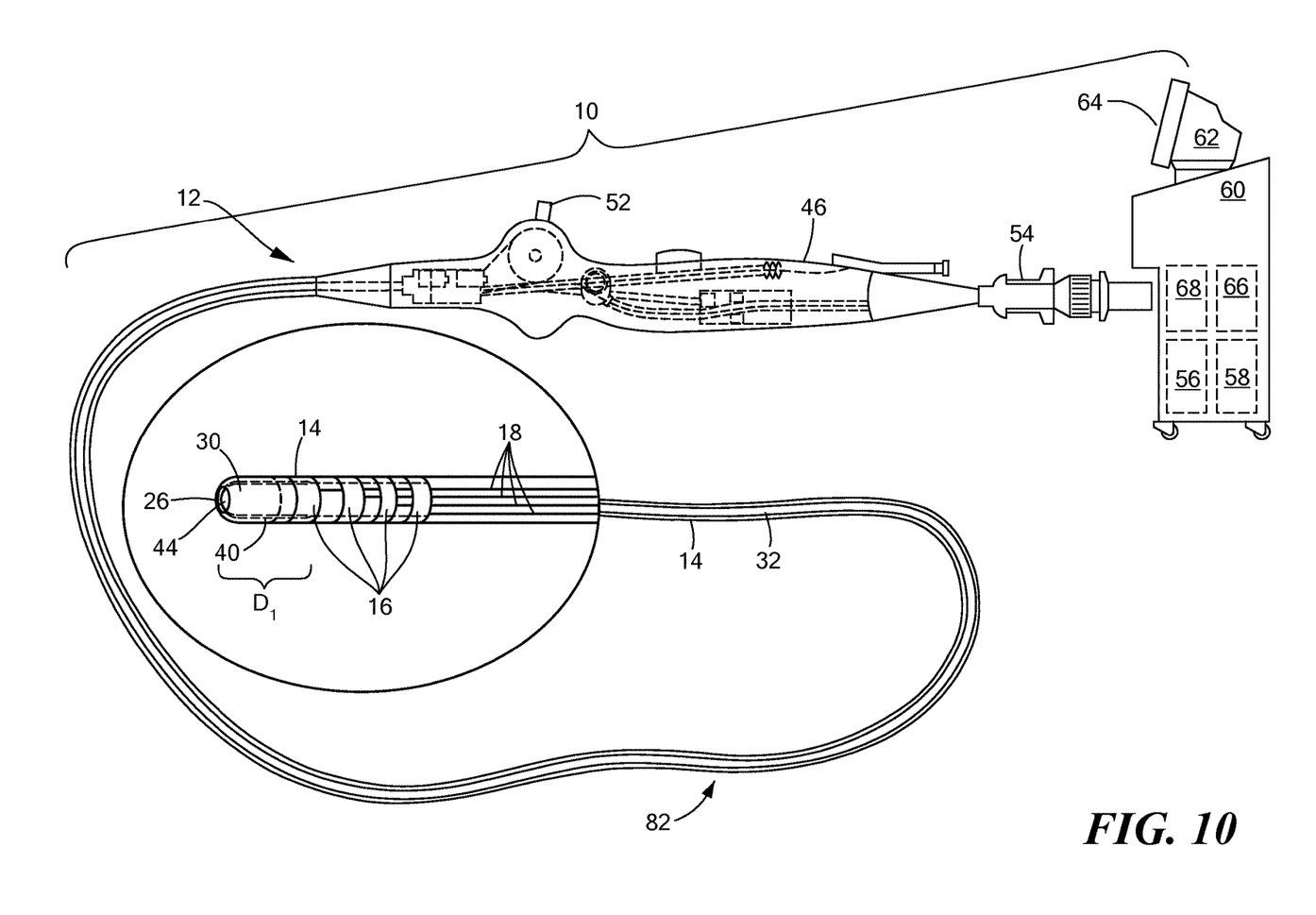
FIG. 10 shows a second embodiment of a system including a mapping sleeve and a treatment device according to the present invention.

Referring now to FIGS. 6-8, cross-sectional views of a first, second, and third embodiment of a mapping sleeve 14 are shown. These cross-sectional views illustrate the disposition of the electrode wires 18 within the mapping sleeve 14. In the embodiment shown in FIG. 6, the electrode wires 18 are disposed between the mapping sleeve 14 and the elongate body 32 of the device 12. Each wire 18 may extend from a mapping electrode 16 at the wire distal region 70 to the console 60 or console component, such as an energy generator 68, computer 62, processor, or the like at the wire proximal region 72. Alternatively, the wire 18 may extend to the handle 46 at the wire proximal region 72. The handle 46, in turn, may be coupled to the console 60 via one or more cables, umbilicals, conduits, or the like. To prevent the wires 18 from becoming entangled with each other or with the device 12 when the sleeve 14 is retracted, the wires 18 may be fused within or affixed to an inner surface 20 of the sleeve 14 between the sleeve 14 and the device 12 or fused within or affixed to an outer surface 24 of the sleeve 14. However, each wire 18 may include an exposed region between the proximal region of the sleeve and the handle, or each wire 18 may be disposed within or encased within a retraction element 42 (as shown in FIG. 9), or each wire 18 may be fused within or affixed to an inner 20 or outer 24 surface of the sleeve 14 for a length of the elongate body 32, to the handle 46 or proximate the handle 46 (as shown in FIG. 10). In FIG. 7, the sleeve 14 may include a dedicated wire lumen 22 that continues along a length of the sleeve 44, from the mapping electrodes 16 to the proximal edge 74 of the sleeve 14. The wire lumen 22 may have a circular cross section; however, in an alternative space-saving configuration, the wire lumen 22 may have an elongate, hemispherical, or other non-round cross section. The wires 18 may be contained within the lumen 22 and thus directed in a bundle along the mapping sleeve 14. In FIG. 8, the wires 18 may be disposed within extrusion layers 76 of the sleeve 14. For example, the sleeve 14 may include two or more layers 76 that are coextruded during the manufacturing process with the wires 18 disposed between them. In the non-limiting embodiment shown in FIG. 8, the sleeve 14 may include an inner layer 76' and an outer layer 76", between which the wires 18 extend from the mapping electrodes 16 at the distal region 70 to the proximal edge 74 of the sleeve 14.

Referring now to FIG. 9, a proximal region 38 of a mapping sleeve 14 of FIG. 1 is shown. The sleeve 14 may include one or more cables, cords, wires, or other retraction elements 42. As used herein, the term "retraction element" refers to any structure coupled to the mapping sleeve 14 that is used to retract the mapping sleeve 14, connect the mapping sleeve 14 to the handle 46 and/or console 60 or console component, and/or house the wires 18 proximal of the mapping sleeve 14. Although a user may manually pull the mapping sleeve 14 portion that is external to the patient to retract the mapping sleeve 14 from one or more treatment elements 48 within the patient, the mapping sleeve 14 is not itself referred to as a "retraction element." The one or more retraction elements 42 may be in communication with one or more actuators, wheels, knobs, or other control elements 52 for retracting the mapping sleeve 14. For example, rotation of a knob or wheel 52 within the handle 46 may wind up a portion of the retraction element 42, thereby retracting the mapping sleeve 14 from the one or more treatment elements 48 of the device 12. Alternatively, the user may pull on the one or more retraction elements 42 to retract the mapping sleeve 14 manually.

The one or more retraction elements 42 may be coupled to an outer surface 24 of the sleeve 14. Further, the retraction element 42 may be composed of the same material as the sleeve 14 (and, indeed, may be formed with the sleeve during manufacturing), or it may be composed of another material such as one or more biocompatible polymers or metals. The proximal region 38 of the sleeve 14 may define a proximal edge 74, and the retraction elements 42 may be coupled to the sleeve 14 at or near this proximal edge 74. Further, at least a portion of the proximal region 38 of the sleeve 14 near the proximal edge 74 may be reinforced with an extra layer of material, an integrated ring or cuff 78 of a material having a higher durometer than the sleeve material, or the like, to strengthen the sleeve against breakage or tearing when the retraction elements 42 are pulled to retract the sleeve 14. Any number of retraction elements 42 may be used. In the non-limiting embodiment shown in FIG. 9, the proximal region 38 of the sleeve 14 may include a tube that is composed of the same material as and integrated with the mapping sleeve 14. Further, the tube 42 may define a lumen 80 within which the wires 18 are disposed. If the sleeve 14 includes a dedicated wire lumen 22, the wire lumen 22 may be substantially coaxial with the lumen 80 of the retraction element 42. Alternatively, as shown in FIG. 9, the wires 18 may be fused to an inner surface 20 of the sleeve 14 and enter the retraction element 42 lumen 80 as a bundle. The retraction element 42 may also serve as a connector between the mapping sleeve 14 and console 60 or console element, such as the energy generator 68 or computer 62 (as shown in FIG. 1). Further, the wires 18 may be contained within the retraction element 42 until the point of connection with, for example, the console 60 or console component, which may keep the wires 18 together and prevent snagging or damage. Alternatively, the wires 18 may be independent of the retraction element 42 for a distance proximal the console 60 or console component. Configuring the wires 18 to be directly connectable to the console 60 or console element instead of the handle 46 allows the mapping sleeve 14 to be used as an accessory that is independent of the device 12 and easily adds mapping functionality to an existing device 12.

Figure 11A:
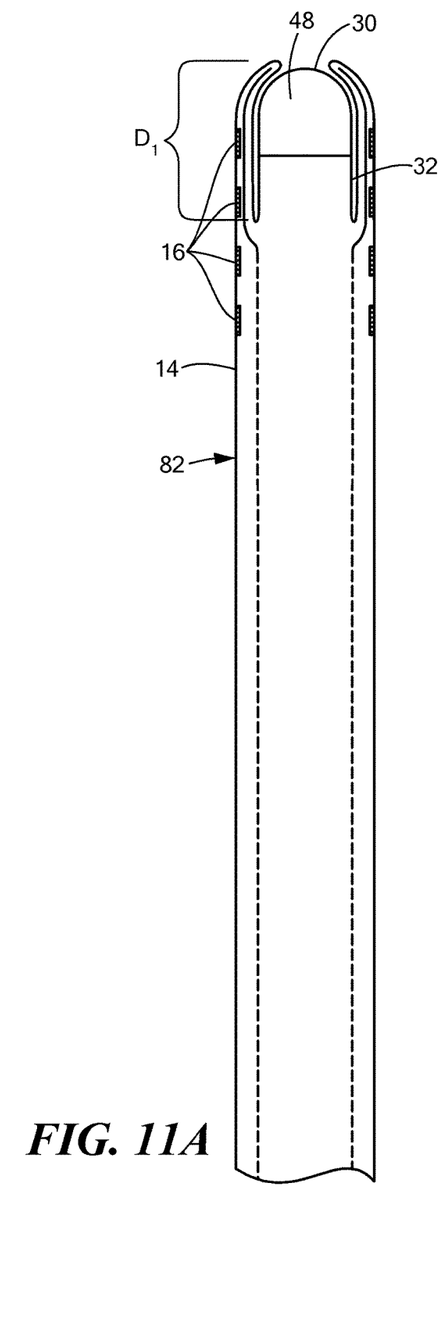
FIG. 11A shows a cross-sectional view of the treatment device of FIG. 10, the mapping sleeve disposed over at least a portion of the distal region of the treatment device, such that the treatment element is covered by the mapping sleeve.
Figure 11B:
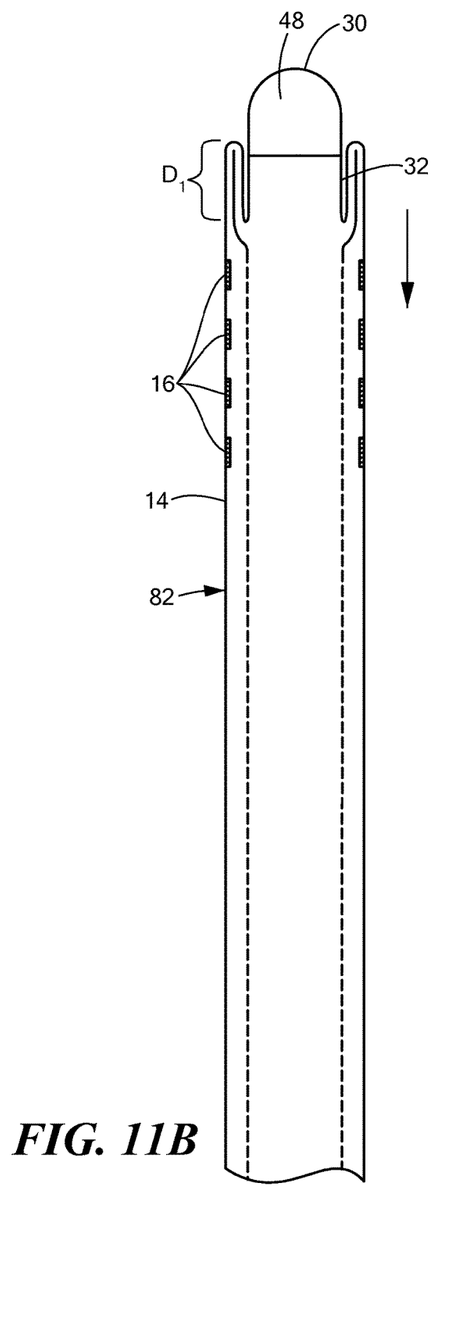
FIG. 11B shows a cross-sectional view of the treatment device of FIG. 10, with the mapping sleeve retracted to expose the treatment element.

Referring now to FIGS. 10-11B, a second embodiment of a system including a mapping sleeve 14 and a treatment device 12 according to the present invention and a cross-sectional view of the mapping sleeve 14 and ablation device 12 are shown. The system 10 of FIG. 10 may generally be same as the system 10 shown and described in FIGS. 1-9. Further, the use of the treatment device 12 and mapping sleeve 14, and disposition of the mapping electrodes 16 and mapping electrode wires 18, of FIGS. 10-11B may generally be the same as that shown and described in FIGS. 1-9. However, the mapping sleeve 14 of the embodiment of FIGS. 10-11B may be integrated with at least a portion of the device 12. For example, the mapping sleeve 14 may be composed of a biocompatible material similar to that of which the elongate body 32 of the device 12 is composed, but the mapping sleeve 14 material may have a lower durometer than the elongate body 32 material, such that the mapping sleeve 14 forms an outer layer that is softer or more flexible than the elongate body 32. For simplicity, the mapping sleeve 14 and elongate body 32 of the device 12 will still be referred to separately; in practice, however, the sleeve 14 and elongate body 32 will together comprise a medical device 12 with integrated mapping and ablation functionality. That is, the mapping sleeve 14 and elongate body 32 will be integrated into a single elongate, flexible body 82 extending from the handle 46.

As described above, the mapping sleeve 14 as shown in FIGS. 10-11B may be integrated with the elongate body 32 from, for example, the handle 46 to a location within the distal region 36 of the elongate body 32 that is a distance $D_1$ proximal from the one or more treatment elements 48 (for example, ablation electrodes that may be at or proximate the distal tip 30 of the elongate body 32). Along distance D1 to the distal tip 30 of the elongate body 32, the mapping sleeve 14 may be separated from the elongate body 32 and form a discrete layer over at least the portion of the elongate body 32 that includes the treatment elements 48 (as shown in FIG. 11A). The mapping sleeve 14 material along the length of distance $D_1$ may be folded in on itself, allowing the mapping sleeve 14 to be retracted form the treatment element 48. This feature is shown in the cross-sectional view of FIGS. 11A and 11B. Further, the distal tip 26 of the mapping sleeve 14 may include an opening 44, for example, as shown and described in FIGS. 6-8.

Once the mapping sleeve 14 is used to record mapping signals from the target tissue (for example, electrocardiogram signals), the mapping sleeve 14 may be retracted from the one or more treatment elements 48 by sliding the softer mapping sleeve 14 layer over the firmer elongate body 32, toward the handle 46 (as shown in FIG. 11B). For example, a user may perform this step by hand, without using actuators 52 within the handle 46. The distance $D_1$ over which the mapping sleeve 14 is not integrated with the elongate body 32 may be a function of both the distance over which the one or more treatment elements 48 are disposed in the distal region 36 of the elongate body 32, and the durometer difference between the mapping sleeve 14 and the elongate body 32. As the mapping sleeve 14 is retracted from the one or more the treatment elements 48, the distance $D_1$ may be reduced, as shown in FIG. 11B. Mapping sleeve wires 18 may be connected to the handle 46 or they may be connected directly the console 60 or console element, as described above, for example, regarding FIG. 9.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for performing mapping and ablation, the system comprising:
   a power generator;
   an ablation device including a handle, an ablation element, and an elongate body defining a distal portion, a proximal portion coupled to the handle, and a longitudinal axis, the ablation element being located on the distal portion of the elongate body and coupled directly to the power generator;
   a resilient mapping sleeve disposable about at least the ablation element of the distal portion of the ablation device, the mapping sleeve defining a distal portion, a proximal portion, an inner surface, an outer surface, and a primary lumen having a longitudinal axis;
   a plurality of mapping electrodes disposed on the outer surface of the mapping sleeve, each of the plurality of mapping electrodes including an electrode wire that is coupled directly to the power generator; and
   a tubular retraction element coupled to the proximal portion of the mapping sleeve and defining a lumen and a longitudinal axis, at least a portion of the electrode wire of each of the plurality of mapping electrodes being located within the lumen of the retraction element, the longitudinal axis of the retraction element being offset from the longitudinal axis of the mapping sleeve,
   exerting a pull force on the retraction element toward the proximal portion of the elongate body pulling the mapping sleeve away from and exposing the ablation element of the ablation device.

2. The system of claim 1, wherein the distal portion of the mapping sleeve includes an exit opening sized to allow at least a portion of the distal portion of the elongate body to pass therethrough.

3. The system of claim 1, wherein the distal portion of the mapping sleeve defines an exit opening.

4. The system of claim 3, wherein at least a region of the elongate body and the ablation element protrude from the exit opening of the mapping sleeve when the mapping sleeve is retracted.

5. The system of claim 4, wherein the mapping sleeve further defines a secondary lumen having a longitudinal axis, the longitudinal axes of the primary lumen and secondary lumen being substantially parallel.

6. The system of claim 5, wherein at least a portion of the electrode wire of each of the plurality of mapping electrodes is coupled to an inner surface of the mapping sleeve primary lumen, printed onto the outer surface of the mapping sleeve, or disposed within the secondary lumen.

7. A system for performing mapping and ablation, the system comprising:
   a power generator;
   an ablation device including a handle, a treatment element, and an elongate body defining a distal portion, a proximal portion, and a length, the treatment element being located on the distal portion of the elongate body and coupled directly to the power generator;
   a mapping sleeve disposable about at least the treatment element, the mapping sleeve having a length that is less than the length of the elongate body, the mapping sleeve defining a longitudinal axis;
   a plurality of mapping electrodes disposed on the outer surface of the mapping sleeve, each of the plurality of mapping electrodes including a wire that is directly coupled to the power generator; and
   a retraction element defining a proximal end, a distal end, a longitudinal axis, and a length between the proximal end and the distal end, the distal end being coupled to the proximal region of the mapping sleeve, the longitudinal axis of the retraction element being parallel to and offset from the longitudinal axis of the mapping sleeve, exerting a pull force on the proximal end of the retraction element toward the handle pulling the mapping sleeve away from and exposing the treatment element of the ablation device.

* * * * *